(12) United States Patent
Shoaf

(10) Patent No.: US 7,306,942 B1
(45) Date of Patent: Dec. 11, 2007

(54) ENDOSPORE DETECTOR

(76) Inventor: Antony R. Shoaf, 2386 Horseshoe Neck Rd., Lexington, NC (US) 27295

( * ) Notice: Subject to any disclaimer, the term of this patent is extended or adjusted under 35 U.S.C. 154(b) by 171 days.

(21) Appl. No.: 10/857,760

(22) Filed: May 28, 2004

Related U.S. Application Data

(62) Division of application No. 10/035,277, filed on Nov. 19, 2001, now Pat. No. 6,815,178.

(51) Int. Cl.
*C12M 1/34* (2006.01)
*G01N 21/76* (2006.01)

(52) U.S. Cl. ............... 435/288.7; 422/52; 422/82.05; 250/573; 250/435; 250/461.2

(58) Field of Classification Search .............. None
See application file for complete search history.

(56) References Cited

U.S. PATENT DOCUMENTS

| | | | | |
|---|---|---|---|---|
| 3,671,450 | A | 6/1972 | Rauhut et al. | 252/700 |
| 4,193,963 | A | 3/1980 | Bruening et al. | 422/52 |
| 4,604,364 | A * | 8/1986 | Kosak | 436/501 |
| 4,665,022 | A * | 5/1987 | Schaeffer et al. | 435/7.72 |
| 5,173,264 | A | 12/1992 | Zaromb | 422/88 |
| 5,340,714 | A | 8/1994 | Katsilometes | 435/6 |
| 5,360,728 | A * | 11/1994 | Prasher | 435/189 |
| 5,773,710 | A * | 6/1998 | Squirrell | 73/28.01 |
| 5,792,621 | A | 8/1998 | Verostko et al. | 435/14 |
| 5,837,195 | A | 11/1998 | Malek et al. | 422/52 |
| 5,885,529 | A | 3/1999 | Babson et al. | 422/65 |
| 6,087,183 | A | 7/2000 | Zaromb | 436/178 |
| 6,103,534 | A * | 8/2000 | Stenger et al. | 436/63 |
| 6,406,667 | B1 | 6/2002 | Singh et al. | 422/52 |
| 6,461,570 | B2 | 10/2002 | Ishihara et al. | 422/65 |
| 6,485,962 | B1 | 11/2002 | Tabacco et al. | 435/288.7 |
| 6,767,733 | B1 | 7/2004 | Green | 435/288.5 |
| 6,803,238 | B1 | 10/2004 | Eggers | 436/518 |

OTHER PUBLICATIONS

Chemiluminescence Emission during Reactions between Superoxide and Selected Aliphatic and Aromatic Halocarbons in Aprotic Media; Antony R. Shoaf, Ali U. Shaikh, Joseph H. Ford, William C. Carlson and Richard H. Steele; Copyright 1996 by John Wiley & Sons, Ltd; J Biolumin Chemilumin 1996; 11: pp. 9-22.

Extraction and Analysis of Superoxide Free Radicals ($\cdot O_2^-$) from Whole Mammalian Liver; Antony R. Shoaf, Ali U. Shaikh, Raymond D. Harbison and Ocsar Hinojosa; Copyright 1991 by John Wiley & Sons, Ltd.; Journal of Bioluminescence and Chemiluminescence vol. 6 , pp. 87-96 (1991).

(Continued)

*Primary Examiner*—David Redding

(57) ABSTRACT

The invention herein provides for the detection of certain calcium containing endospores, and particularly pertains to the detection of bacillus anthracis by first chelating calcium ions of said endospores and then reacting the chelated calcium ions with aequorin to generate a light pulse which can then be detected by a standard liquid scintillation spectrometer.

**14

OTHER PUBLICATIONS

Welcome to HKUST Calcium-Aequorin Imaging Laboratory, Biology, Hong Kong University of Science & Technology; Image Photon Detectors and Data Acquisition stations; three (3) pages; last updated Oct. 18, 2001.
Science Wares; Photon Imaging System Description; Copyright 2000 Science Wares; five (5) pages; last updated Oct. 27, 2000.
Science Wares; Calcium Imaging Publications; Copyright 1998 Science Wares; one (1) page; last updated Mar. 18, 1998.

Chelation Characteristics of Calcium in Relation to Water Binding and Heat Resistance of Bacterial Endospores; K. S. Rahan and N. Grecz; Spong Research 1997, vol. 2; pp. 527-543.

Effect of calcium chelators on the $Ca^{2+}$-dependent luminescence of aequorin; Osamu Shimomura and Akemi Shimomura; Biochem. J. (1984) 221; 907-910.

* cited by examiner

ENDOSPORE DETECTOR

This application is a divisional of application Ser. No. 10/035,277 filed Nov. 19, 2001, now U.S. Pat. No. 6,815,178.

FIELD OF THE INVENTION

The invention herein pertains to detection devices and methods, and particularly pertains to the detection of calcium containing endospores which are delivered from an airborne state to a reaction vessel.

DESCRIPTION OF THE PRIOR ART AND OBJECTIVES OF THE INVENTION

Certain light emitting photoproteins, such as those isolated from the jellyfish Aequorea aequoorea, perform a natural reaction when allowed to mix with calcium ion, $Ca^{++}$, with the resultant production of light or chemiluminescence. Such calcium reporter photoproteins are known as aequorin.

Many gram-positive bacteria such as those of the genera Clostridium and Bacillus form specialized "resting" cells called endospores. Endospores are highly durable dehydrated cells with thick walls and additional layers. They are formed internal to the bacterial cell membrane.

When released into the environment, endospores can survive extreme heat, lack of water and exposure to many toxic chemicals and radiation. Most of the water present in the spore cytoplasm is eliminated. Such endospores do not generally carry out metabolic reactions. A strikingly large amount of an organic acid called dipicolinic acid (found in the cytoplasm) is accompanied by a large number of calcium ions. Calcium ions ($Ca^{++}$) are combined with the dipicolinic acid as seen below:

[chemical structure]

The calcium-dipicolinic acid complex represents about ten percent of the dry weight of the endospore. As would be understood, such endospores can readily become airborne. If present in an area of human occupancy, such as an office building, home or the like, certain endospores can be life threatening when present through inadvertence, accident or deliberately introduced by bioterrorists.

Liquid scintillation spectrometers are commonly used to measure radioisotopes such as in medical research when used in an out of coincidence mode it senses both analog signals from two photomultiplier tubes to thereby act as a photon (light pulse) counter.

While various types of detection methods for certain deadly endospores such as bacillus anthracis (anthrax) are known, these methods generally consist of collecting specimens from office buildings, homes or the like and thereafter delivering them to a laboratory for analysis. While such laboratory analyses may be very accurate, they are time consuming in that the collection, delivery and analytical work can take several days. Thus, those unfortunate enough to be infected with deadly endospores such as anthrax may have their medical condition diagnosed too late to save their lives.

Therefore, in view of the need for a speedy and continuous method of detecting anthrax and other calcium containing endospores which may be, for example, airborne in public buildings, the present invention was conceived and one of its objectives is to provide a device and method whereby bacillus anthracis and other calcium containing endospores can be easily and inexpensively detected.

It is an objective of the invention to provide a device for detecting certain calcium containing endospores when used as weapons or when naturally occurring such as near cattle or other animals.

It is another objective of the present invention to provide a device and method for detecting certain calcium containing endospores which is easy to operate and requires little specialized training.

It is yet another objective of the present invention to provide a method for detecting calcium containing endospores which is relatively inexpensive to operate continuously for twenty-four hours a day.

It is still another objective of the present invention to provide a method of detecting calcium containing endospores utilizing a chelating agent and natural aequorin as derived from jellyfish.

It is still another objective of the present invention to provide a method of detection of calcium containing endospores utilizing a standard scintillation spectrometer.

Various other objectives and advantages of the present invention will become apparent to those skilled in the art as a more detailed description is set forth below.

SUMMARY OF THE INVENTION

The aforesaid and other objectives are realized by providing a scintillation spectrometer with a reaction vessel containing a chemiluminescent liquid. The reaction vessel is joined to an air pump by an intake conduit. The air pump delivers air from an office, room or the like through a conventional particulate filter capable of excluding particles greater than 20 μM, and into the chemiluminescent liquid. Calcium containing endospores such as bacillus anthracis then mix with the chemiluminescent liquid in which the calcium ions contained therein are first chelated. The chelated calcium ions then react with the chemiluminescent photoprotein aequorin in the chemiluminescent liquid and produce light. This chemiluminescent reaction emits photons of light which, in one embodiment are directed through the walls of the glass reaction vessel, through a light guide and into photomultiplier tubes where they are intensified. Analog signals resulting therefrom are then delivered to a ratemeter which in turn delivers corresponding electrical signals to a chart recorder and, if desired, to a printer.

In a second embodiment of the invention the spectrometer converts the light pulses to a digital signal which are sent to a personal computer (PC) whereby the signals can be read in real time on the PC monitor.

DETAILED DESCRIPTION OF THE PREFERRED EMBODIMENTS AND OPERATION OF THE INVENTION

Figure 1:
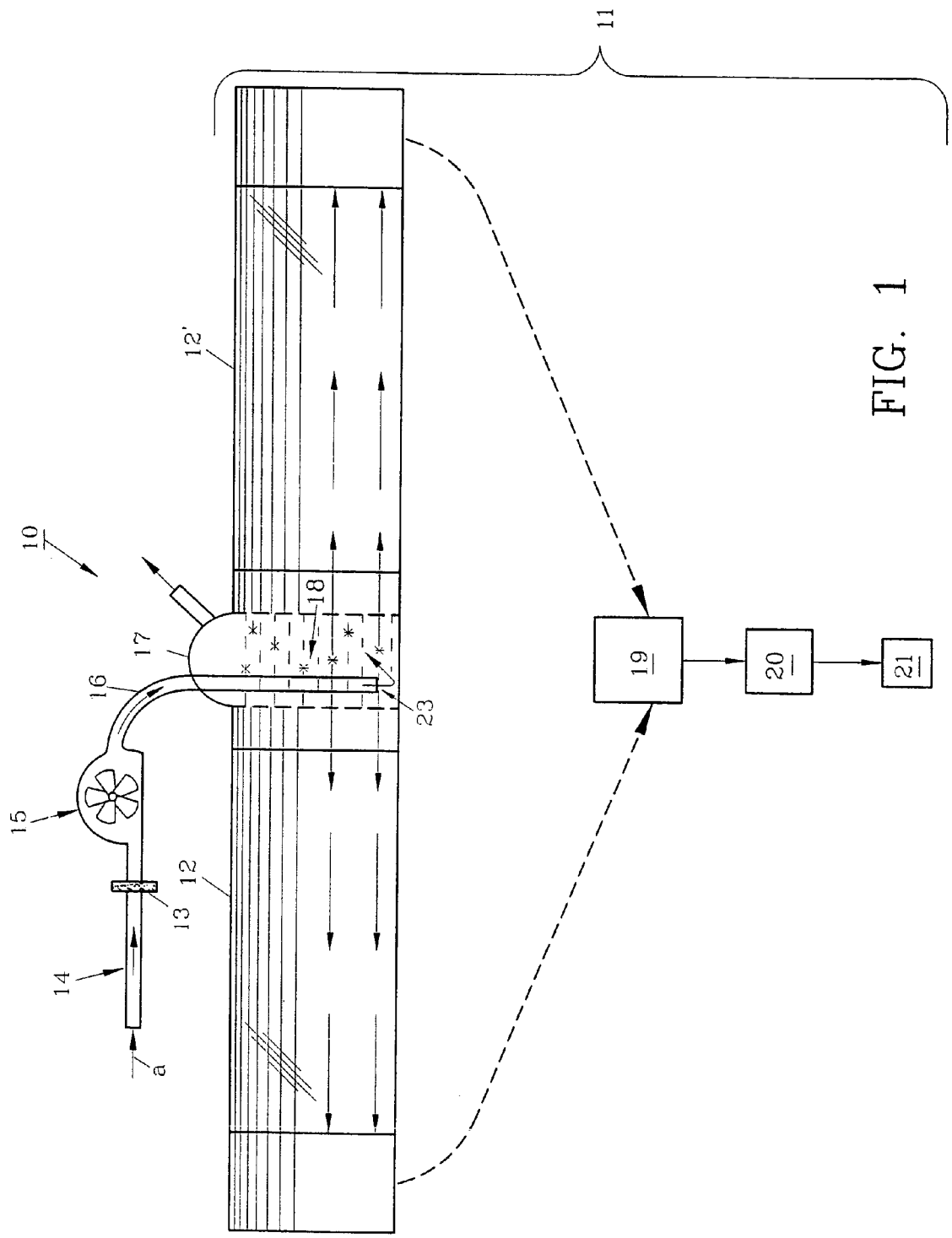
FIG. 1 shows a schematic representation of the preferred detection device of the invention.

For detection of endospores of Bacillus anthracis capable of causing a disease, commonly known as anthrax, the preferred method is demonstrated in FIG. 1 whereby air with calcium containing endospores is represented by arrow a. Preferred detection device 10 for detecting endospores is shown in schematic fashion utilizing a model 3320 Packard Liquid Scintillation spectrometer 11 as sold by Packard Instrument Company of Downers Grove, Ill. operated in an out-of-coincidence mode at the preferred ambient temperature of 22° C. Detection device 10 is used for continuous monitoring of analog signals received from each of the photomultiplier tubes 12, 12'.

As seen, calcium containing endospores are first directed through particulate filter 13 (capable of removing particle size of 20 μM) of air tube 14 by air pump 15 which then forces the filtered air through intake conduit 16 and on into reaction vessel 17. Terminal end 23 of intake conduit 16 is shown submerged in chemiluminescent liquid 18. Conventional particulate filter 13 excludes particles greater than 20 μM (1 μM=0.000001M).

As shown in FIG. 1, reaction vessel 17 contains preferred chemiluminescent liquid 18 which is prepared as follows:

7.455 g. of potassium chloride,
1.047 g. 3-[-Morpholino]propanesulfonic acid, and
19.01 mg. ethylenediamine tetraacetate, tetrasodium salt, (EDTA)

are dissolved in 1 liter of water and are mixed to form the preferred buffer solution.

Next,
1 g. aequorin* and
100 ml of the buffer solution above are mixed and approximately 20 ml of this preferred chemiluminescent liquid 18 are placed in reaction vessel 17. Preferably naturally occurring aequorin is used but purified extracts of natural aequorin or synthetically prepared aequorin may also be used.

*Natural aequorin can be purchased from Sigma Co. of St. Louis, Mo. 63178.

Reaction vessel 17, as manufactured by Fisher Scientific of Pittsburgh, Pa. 15275, is preferably made of quartz while borosilicate low potassium glass may also be used. Reaction vessel 17 preferably has a height of 61 mm and an outside diameter of 28 mm. Air pump 15 as shown preferably provides a 12.5 L/min air flow to reaction vessel 17 through Teflon (trademark of E.I. DuPont DeNemours and Co., Wilmington, Del.), intake conduit 16 which has a diameter of 4 mm. As would be further understood from FIG. 1, light pulses from reaction vessel 17 are directed through photomultiplier tubes 12, 12' and are directed to ratemeter 19, preferably a model 280A as manufactured by Packard Instrument Company. The light pulses generated in reaction vessel 17 are a result of the chemical reactions shown below:

$Ca^{++}$ endospores+EDTA - - - - - >$Ca^{++}$ $Ca^{++}$+aequorin - - - - - >photons of light Signals are sent from ratemeter 19 as illustrated schematically in FIG. 1 to Honeywell Electronik strip chart recorder 20 and on to Monroe digital printer 21. Separate count per minute readings can be then printed as desired. While a model 3320 Packard Instrument liquid scintillation spectrometer is preferred, various other types of spectrometers could likewise be used.

Standard scintillation spectrometer 11 as seen in FIG. 1 includes photomultiplier tubes 12, 12' which are preferably manufactured by EMI Thorn Company, (England) as catalogue No. 9635QB. Tubes 12, 12' are sensitive to the wavelengths of light corresponding to the maximum wavelength of light emissions provided herein.

Figure 2:
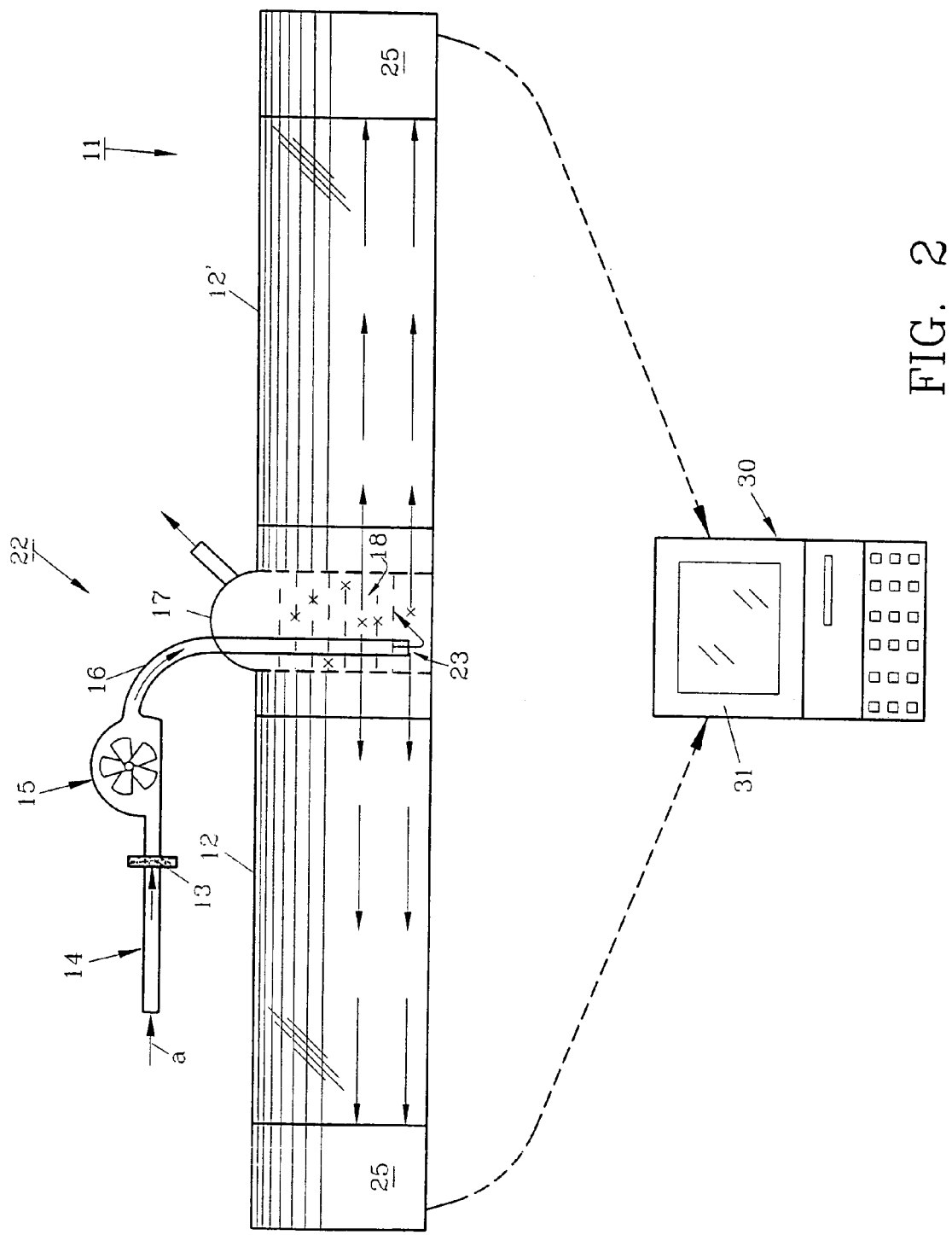
FIG. 2 demonstrates schematically an alternate embodiment of the invention as shown in FIG. 1.

In an alternate embodiment, detection device 22 as shown in FIG. 2 includes Packard spectrometer 11 which has been modified as schematically shown whereby its analog to digital convertor 25 is utilized and the resulting digital signal is fed to PC 30. PC monitor 31 can then be used to continuously monitor the activity of reaction vessel 17 in real time.

While the preferred detection device 10 as shown in FIG. 1 is suitable for use as a table or desktop setup, device 10 could also be made portable and carried by a person. In this event the device would be miniaturized to some degree and have its own power source such as conventional batteries. A miniaturized version (not seen) may have dimensions of about 60 cm by 30 cm by 30 cm for portability.

The illustrations and examples provided herein are for explanatory purposes and are not intended to limit the scope of the appended claims.

I claim:

1. A product for detecting calcium containing endospores comprising: a reaction vessel, an air pump, an air intake conduit, said air pump communicating with said air intake conduit, a chemiluminescent liquid, said chemiluminescent liquid contained within said reaction vessel, said air intake conduit submerged within said chemiluminescent liquid, said chemiluminescent liquid comprising aequorin and a calcium chelating agent, a photon counter, said photon counter comprising a photomultiplier and a ratemeter, said photon counter positioned proximate said reaction vessel for sensing photons of light immediately upon occurrence in said reaction vessel, a computer, said photon counter connected to said computer, whereby calcium containing endospores directed into said reaction vessel will immediately react with said chemiluminescent liquid emitting photons of light for detection by said photon counter and reading by said computer.

2. The product of claim 1 wherein said photomultiplier contacts said reaction vessel.

3. The product of claim 1 wherein said calcium chelating agent comprises ethylenediamine tetraacetate, tetrasodium salt.

4. The product of claim 1 wherein said aequorin is extracted from jellyfish.

5. The product of claim 1 wherein said chemiluminescent liquid comprises aequorin dissolved in an ethylenediamine tetraacetate buffer solution.

6. The product of claim 1 wherein said photon counter comprises a liquid scintillator spectrometer.

7. The product of claim 1 wherein said photon counter comprises a pair of photomultipliers.

8. The product of claim 1 wherein said air intake conduit has a diameter of 4 mm.

9. The product of claim 1 wherein said air pump forces air through said air intake conduit at approximately 12.5 liters per minute.

10. A product for detecting calcium containing endospores comprising: a reaction vessel, an intake conduit, said intake conduit in fluid communication with said reaction vessel, a chemiluminescent liquid, said chemiluminescent liquid contained within said reaction vessel, an air pump, said air pump mounted proximate said intake conduit, said conduit submerged within said chemiluminescent liquid, a liquid scintillation spectrometer, said liquid scintillation spectrometer proximate said reaction vessel for immediately detecting photons of light as they occur in said reaction vessel, said scintillation spectrometer comprising a pair of photomultipliers, a ratemeter, said photomultipliers in electrical communication with said ratemeter, a chart recorder, said chart recorder in electrical communication with said ratemeter, a printer, said printer in electrical communication with said chart recorder, said chemiluminescent liquid comprising aequorin, a chelating agent, said chelating agent mixed with said aequorin, whereby endospores containing calcium forced by said air pump into said chemiluminescent liquid will immediately react with said aequorin to generate light pulses for detection by said liquid scintillation spectrometer.

11. The product of claim 10 wherein said chelating agent comprises ethylenediamine tetraacetate, tetrasodium salt.

12. A product for detecting calcium containing endospores comprising: a reaction vessel, a chemiluminescent liquid, said chemiluminescent liquid contained within said reaction vessel, an air intake conduit, said air intake conduit comprising a terminal end, said terminal end submerged within said chemiluminescent liquid, said chemiluminescent liquid comprising aequorin and a calcium chelating agent, a photon counter, said photon counter positioned proximate said reaction vessel to sense photons of light immediately upon occurrence in said reaction vessel, whereby calcium containing endospores directed through said air intake conduit and into said chemiluminescent liquid will immediately react with said chemiluminescent liquid emitting photons of light for detection.

13. The product of claim 1 further comprising an air tube, a particulate filter, said particulate filter contained within said air tube and said air tube communicating with said air pump.

14. The product of claim 12 further comprising an air tube, a particulate filter, said particulate filter contained within said air tube and said air tube communicating with said air pump.

* * * * *